United States Patent
McCrory

[11] Patent Number: 5,951,599
[45] Date of Patent: Sep. 14, 1999

[54] OCCLUSION SYSTEM FOR ENDOVASCULAR TREATMENT OF AN ANEURYSM

[75] Inventor: Jennifer J. McCrory, Boston, Mass.

[73] Assignee: Scimed Life Systems, Inc., Maple Grove, Minn.

[21] Appl. No.: 08/890,488

[22] Filed: Jul. 9, 1997

[51] Int. Cl.⁶ .................................................. A61M 29/00
[52] U.S. Cl. ........................... 623/1; 606/108; 606/198; 623/12
[58] Field of Search ................................ 606/1, 108, 198, 606/200; 623/1, 12

[56] References Cited

U.S. PATENT DOCUMENTS

| | | |
|---|---|---|
| 4,416,028 | 11/1983 | Eriksson et al. . |
| 4,577,631 | 3/1986 | Kreamer . |
| 4,650,466 | 3/1987 | Luther . |
| 4,790,819 | 12/1988 | Li et al. . |
| 4,921,484 | 5/1990 | Hillstead . |
| 4,994,071 | 2/1991 | MacGregor . |
| 5,034,001 | 7/1991 | Garrison et al. . |
| 5,413,598 | 5/1995 | Moreland . |
| 5,464,449 | 11/1995 | Ryan et al. . |
| 5,571,173 | 11/1996 | Parodi . |
| 5,609,628 | 3/1997 | Keranen . |
| 5,713,917 | 2/1998 | Leonhardt et al. ...................... 606/198 |
| 5,749,919 | 5/1998 | Blanc ...................................... 606/198 |

FOREIGN PATENT DOCUMENTS

| | | |
|---|---|---|
| 0 547 530 A1 | 6/1991 | European Pat. Off. . |
| 0 815 806 A2 | 1/1998 | European Pat. Off. . |
| WO 95/17859 | 7/1995 | WIPO . |
| WO 96/14027 | 5/1996 | WIPO . |
| WO 96/17645 | 6/1996 | WIPO . |
| WO 97/01368 | 6/1996 | WIPO . |

OTHER PUBLICATIONS

Portion of Article from *Endovascular Neruological Intervention*, pp. 23–24, admitted prior art.

"Endovascular Treatment of Experimental Aneurysms with Liquid Polymers: The Protective Potential of Stents", by Istvan Szikora, M.D., et al., *Neurosurgery*, vol. 38, No. 2, Feb. 1996, pp. 339–346.

*Primary Examiner*—Michael Buiz
*Assistant Examiner*—William Lewis
*Attorney, Agent, or Firm*—Westman, Champlin & Kelly, P.A.

[57] ABSTRACT

An occlusion system treats an aneurysm in a parent vessel. The parent vessel defines a lumen that has a lumen wall. The aneurysm has a neck in communication with the lumen. The occlusion system includes a stent configured for deployment in the parent vessel. The stent has at least a first portion and a second portion. The first portion is permeable to blood flow and is arranged such that, when the stent is deployed, the first portion is spaced from the neck of the aneurysm. The second portion is less permeable to blood flow than the first portion and is arranged such that, when the stent is deployed, the second portion overlies the neck of the aneurysm.

23 Claims, 3 Drawing Sheets

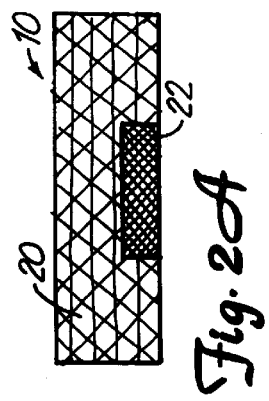
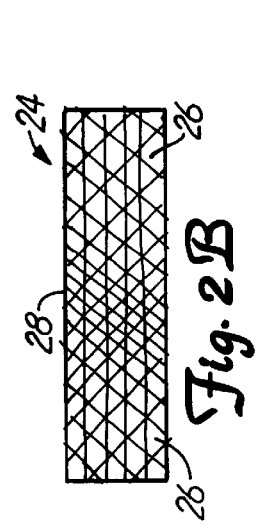
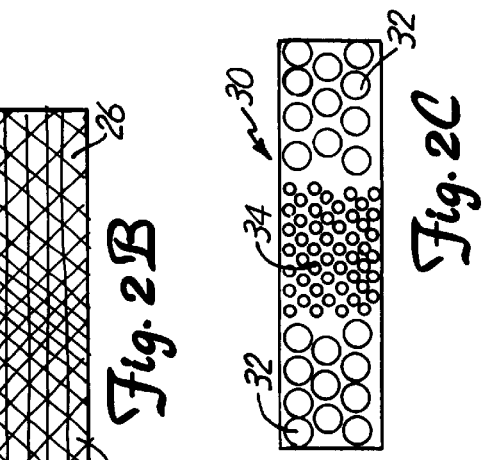
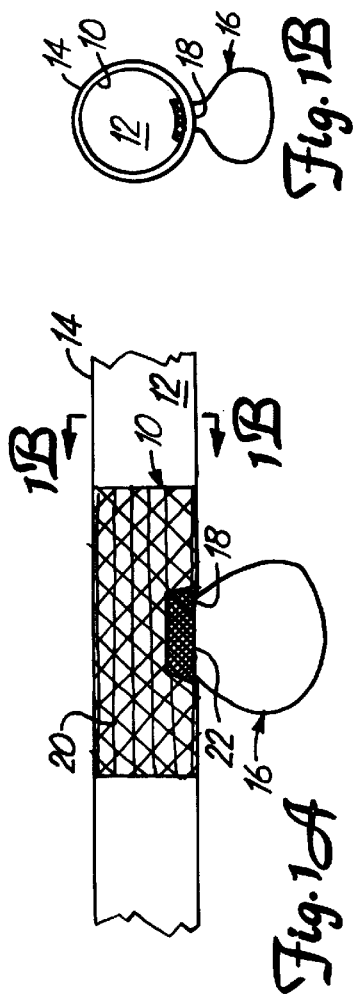
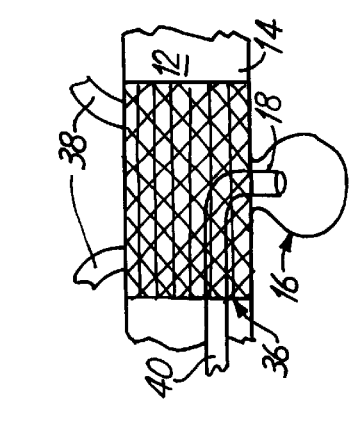
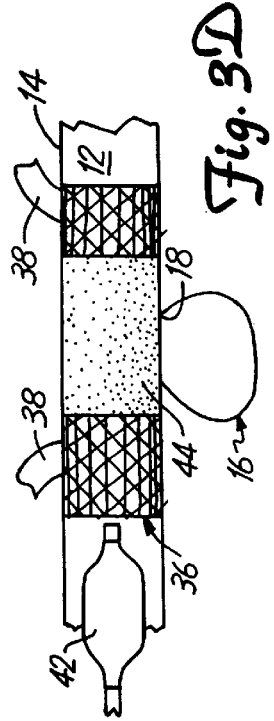
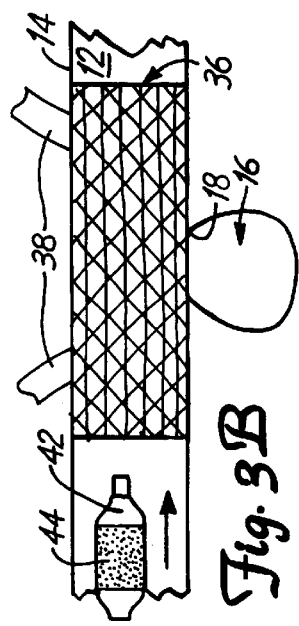
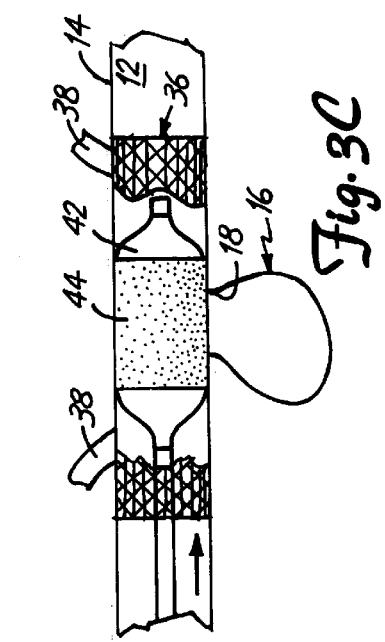

OCCLUSION SYSTEM FOR ENDOVASCULAR TREATMENT OF AN ANEURYSM

BACKGROUND OF THE INVENTION

The present invention deals with a system for treating an aneurysm. More specifically, the present invention deals with an occlusion system deployed in the vasculature containing the aneurysm.

Several methods of treating aneurysms have been attempted, with varying degrees of success. For example, open craniotomy is a procedure by which an aneurysm is located, and treated, extravascularly. This type of procedure has significant disadvantages. For example, the patient undergoing open craniotomy must undergo general anesthesia. Also, the patient undergoes a great deal of trauma in the area of the aneurysm by virtue of the fact that the surgeon must sever various tissues in order to reach the aneurysm. In treating cerebral aneurysms extravascularly, for instances, the surgeon must typically remove a portion of the patient's skull, and must also traumatize brain tissue in order to reach the aneurysm.

Other techniques used in treating aneurysms are performed endovascularly. Such techniques typically involve attempting to form a mass within the sac of the aneurysm. Typically, a microcatheter is used to access the aneurysm. The distal tip of the micro catheter is placed within the sac of the aneurysm, and the microcatheter is used to inject embolic material into the sac of the aneurysm. The embolic material includes, for example, detachable coils. The injection of these types of embolic materials suffer from disadvantages, most of which are associated with migration of the embolic material out of the aneurysm into the parent artery. This can cause permanent and irreversible occlusion of the parent artery.

For example, when detachable coils are used to occlude an aneurysm which does not have a well defined neck region, the detachable coils can migrate out of the sac of the aneurysm and into the parent artery. Further, it is, at times, difficult to gauge exactly how full the sac of the aneurysm is when detachable coils are being injected. Therefore, there is a risk of overfilling the aneurysm in which case the detachable coils also spill out into the parent artery.

Another disadvantage of detachable coils involves coil compaction over time. After filling the aneurysm, there remains space between the coils. Continued hemodynamic forces from the circulation act to compact the coil mass resulting in a cavity in the aneurysm neck. Thus, the aneurysm can recanalize.

Embolic agent migration is also a problem. For instance, where a liquid polymer is injected into the sac of the aneurysm, it can migrate out of the sac of the aneurysm due to the hemodynamics of the system. This can also lead to irreversible occlusion of the parent vessel.

Techniques have been attempted in order to deal with the disadvantages associated with embolic material migration to the parent vessel. Some such techniques, commonly referred to as flow arrest techniques, typically involve temporarily occluding the parent vessel proximal of the aneurysm, so that no blood flow occurs through the parent vessel, until a thrombotic mass has formed in the sac of the aneurysm which helps reduce the tendency of the embolic material to migrate out of the aneurysm sac. However, thrombotic mass can dissolve through normal lysis of blood. Also, in certain cases, it is highly undesirable to occlude the parent vessel even temporarily. Therefore, this technique is, at times, not available as a treatment option. In addition, even occluding the parent vessel may not prevent all embolic material migration into the parent vessel.

Another endovascular technique for treating aneurysms involves inserting a detachable balloon into the sac of the aneurysm using a microcatheter. The detachable balloon is then inflated using embolic material, such as liquid polymer material. The balloon is then detached from the microcatheter and left within the sac of the aneurysm in an attempt to fill the sac of the aneurysm and form a thrombotic mass in any area of the aneurysm not filled by the detachable balloon. However, detachable balloons also suffer disadvantages. For example, detachable balloons, when inflated, typically will not conform to the interior configuration of the aneurysm sac. Instead, the detachable balloon requires the aneurysm sac to conform to the exterior surface of the detachable balloon. Thus, there is an increased risk that the detachable balloon will rupture the sac of the aneurysm.

SUMMARY OF THE INVENTION

An occlusion system treats an aneurysm in a parent vessel. The parent vessel defines a lumen that has a lumen wall. The aneurysm has a neck in communication with the lumen. The occlusion system includes a stent configured for deployment in the parent vessel. The stent has at least a first portion and a second portion. The first portion is permeable to blood flow and is arranged such that, when the stent is deployed, the first portion is spaced from the neck of the aneurysm. The second portion is less permeable to blood flow than the first portion and is arranged such that, when the stent is deployed, the second portion overlies the neck of the aneurysm.

BRIEF DESCRIPTION OF THE DRAWINGS

FIG. 1A is a side view of an occlusion device deployed in a parent vessel and proximate an aneurysm.

FIG. 1B is a transverse cross sectional view of the device shown in FIG. 1A.

FIG. 2A is a side view of one embodiment of the occlusion device shown in FIG. 1A.

FIG. 2B is a side view of a second embodiment of the occlusion device shown in FIG. 1A.

FIG. 2C is a side view of a third embodiment of the occlusion device shown in FIG. 1A.

FIGS. 3A–3D illustrate the application of a covering material to an internal surface of an occlusion device in accordance with the present invention.

DETAILED DESCRIPTION OF THE PREFERRED EMBODIMENTS

Figure 4A:
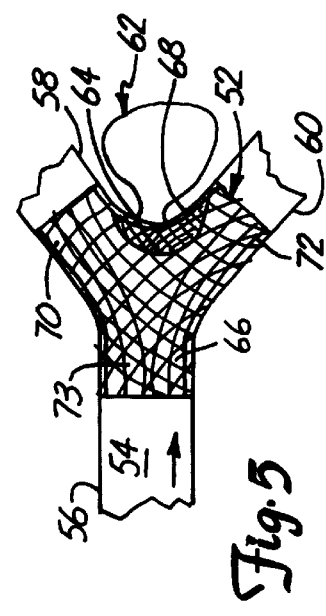
FIGS. 4A–4C illustrate the application of covering material to the outside surface of an occlusion device in accordance with the present invention.

FIGS. 1A and 1B show an occlusion device 10 deployed in the lumen 12 of a vessel 14 proximate an aneurysm 16. In the preferred embodiment, occlusion device 10 is a shape memory mesh device which is delivered to the cite of aneurysm 16 in lumen 12 of parent vessel 14. Device 10 is positioned to reside over neck 18 of aneurysm 16.

Device 10, in the preferred embodiment, has a first portion 20 which is formed of a material having apertures therein so that the material is substantially permeable to blood flow. Occlusion device 10 also preferably includes a second portion 22 which is less permeable to blood flow than portion 20. Occlusion device 10 is deployed in vessel 12 such that second portion 22 is disposed over, and substantially covers, the neck 18 of aneurysm 16. With occlusion device 10 in place, the hemodynamics of the system proximate occlusion device 10 is altered such that blood flow through lumen 12 does not, in any meaningful quantity, enter the sac of aneurysm 16. Instead, occlusion device 10 acts as a flow diverter which substantially contains blood flow within lumen 12 of the parent vessel 14. Since the blood within the aneurysm sac is not circulating with the main blood flow, areas of stagnation are created and the blood in the sac of aneurysm 16 will thrombose.

In the preferred embodiment, occlusion device 10 is meant to remain in lumen 12 permanently. Thus, occlusion device 10 provides a scaffolding for tissue growth, eventually creating a new endolumenal surface inside parent vessel 14 across neck 18 of aneurysm 16.

Figure 5:
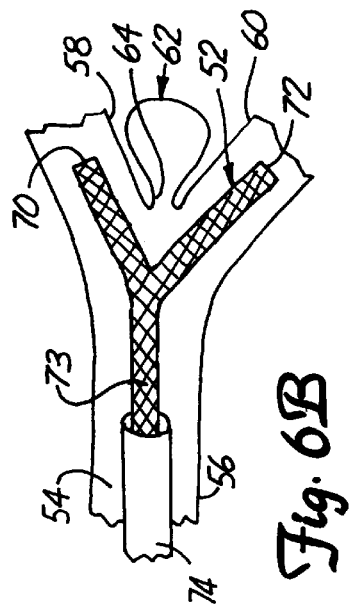
FIG. 5 illustrates an another embodiment of an occlusion device in accordance with the present invention deployed proximate an aneurysm.
Figure 6A:
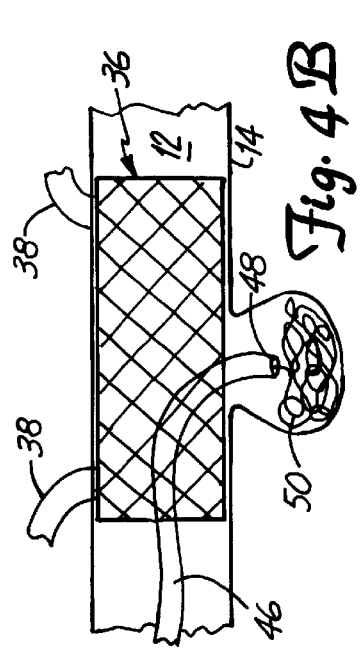
FIGS. 6A–6D illustrate deployment of the occlusion device shown in FIG. 5 in accordance with one aspect of the present invention.
Figure 6B:
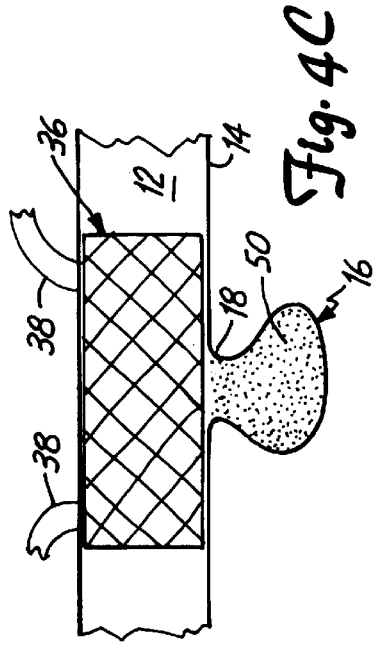
Figure 6D:
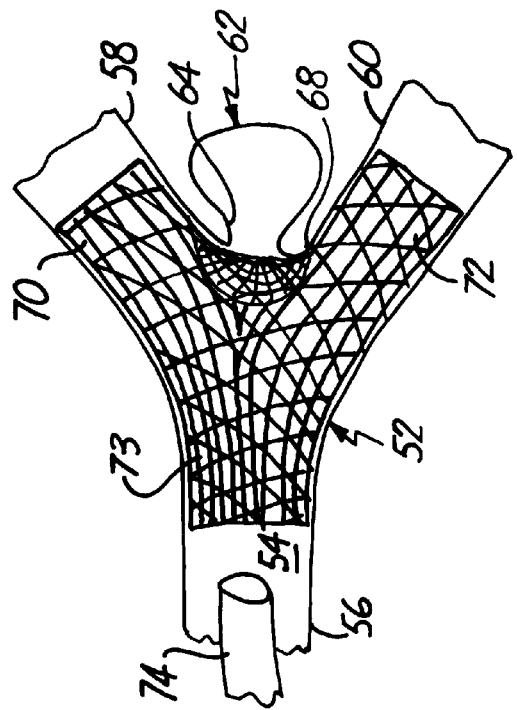

Occlusion device 10 can be deployed in lumen 12 of parent vessel 14 in any number of suitable ways, including that described in greater detail with respect to FIGS. 5–6D. However, in one preferred embodiment, occlusion device 10 is a shape memory tubular device which is capable of residing in a first state, but then transitions to a second state in response to an appropriate stimulus. For example, in one preferred embodiment, occlusion device 10 is a shape memory material which exists in a flexible, and collapsed state when it is below a transition temperature, but expands into a more rigid configuration when it resides in an environment above the transition temperature. The occlusion device 10 is delivered to the vascular region of aneurysm 16 in the more flexible state, below its transition temperature, so that it is soft and flexible enough to pass through tortuous vasculature such as intracranial vasculature. When occlusion device 10 is below its transition temperature, it is preferably not only flexible, but it is capable of being compressed into even a lower profile to enhance its delivery. Device 10 is preferably formed of wires having a diameter and a configuration suitable to achieve the delivery profile desired for any given application. The device 10 is delivered through a catheter.

Once in place adjacent to the neck 18 of aneurysm 16, occlusion device 10 is deployed from the delivery catheter and the temperature is raised from a point below the transition temperature, to a point above the transition temperature. This can be accomplished, for instance, by injecting warm saline, or simply by letting occlusion device 10 warm to body temperature.

Once occlusion device 10 reaches the transition temperature, it expands radially to a predetermined diameter which approximates, and makes contact with, the inner walls of parent vessel 14. The delivery catheter is then removed and occlusion device 10 remains in place.

In accordance with one preferred embodiment of the present invention, occlusion device 10 is formed using small diameter nitinol wire filaments braided to create occlusion device 10, and utilizing the shape memory properties of nitinol to facilitate delivery and deployment as described above. In one embodiment, the nitinol filaments have a diameter of approximately 0.003 inches, or less. This gives occlusion device 10 sufficient flexibility and a very small size which facilitates delivery of occlusion device 10 to intracranial vasculature. Where the device is used to treat other areas of the vasculature (such as an abdominal aortic aneurysm), the wire will have a larger diameter such as in a range of approximately 0.009" to 0.014". The size and shape of the apertures in occlusion device 10, and the density of the filaments in occlusion device 10 are preferably designed to meet the specific application for which they are required.

FIGS. 2A–2C show three preferred embodiments of occlusion device 10 in accordance with the present invention. In FIG. 2A, occlusion device 10 is similar to that shown in FIG. 1A and includes first portion 20 and second portion 22. In the embodiment shown in FIG. 2A, second portion 22 is formed of a material which is substantially impermeable to blood flow, such as a suitable polymer material. Second portion 22 can be woven into the braid of first portion 20 in occlusion device 10, or it can be adhered to the inner or outer surface of occlusion device 10, or it can be attached using any other suitable attachment mechanism.

FIG. 2B shows an alternative embodiment of an occlusion device 24 in accordance with the present invention. Occlusion device 24 is preferably formed of braided filaments, such as braided nitinol filaments. Occlusion device 24 includes first portion 26 and second portion 28. As with occlusion device 10, first portion 26 is substantially permeable to blood flow, while second portion 28 is less permeable to blood flow than first portion 26. In the embodiment shown in 2B, first portion 26 is formed of braided filaments having a first pitch and thus defining apertures of a first size therein. Second portion 28 is formed of braided filaments having a second pitch, different from the first pitch, and thus defining much smaller apertures therein. In this way, simply by changing the pitch of the braid along the length of occlusion device 24, portions 26 and 28 can be formed.

FIG. 2C shows yet another embodiment of the occlusion device 30 in accordance with the present invention. Occlusion device 30 includes first portions 32 and second portion 34. First portions 32 are formed of a mesh-type material having apertures of a first diameter defined therein. Portion 34 is formed of a mesh-type material having apertures of a second diameter, smaller than the diameters of the apertures in the first mesh portions 32. Thus, portion 34 is less permeable to blood flow than portion 32.

In all of the embodiments described herein thus far, by providing an area over the neck 18 of the aneurysm 16 which is less permeable to blood flow than the remainder of the occlusion device, blood flow is diverted away from the aneurysm 16, creating stagnant areas inside the sac of the aneurysm 16. Blood thus thrombose within the sac of the aneurysm 16 and cell growth is promoted over the neck 18 of the aneurysm 16 along the surface of the occlusion device. In the embodiments shown in FIGS. 1A–2C, the aneurysm 16 may first be filled with an embolic material, prior to deployment of the occlusion device. However, in the preferred embodiment, the occlusion devices are used without filling the sac of the aneurysm 16, and simply as a flow diverter avoiding the need for filling the aneurysm 16.

FIGS. 3A–3D illustrate deployment of occlusion device 36 in accordance with another preferred embodiment of the present invention. In the embodiment shown in FIG. 3A, parent vessel 14 has a number of perforating vessels 38 in communication therewith in a region proximate aneurysm 16. Where occlusion device 36 is deployed in vasculature, such as abdominal vasculature, the number of perforating vessels near aneurysm 16 may be much smaller than perforating vessels proximate an intracranial aneurysm. Such perforating vessels are often important in that they supply blood to the distal areas of the brain. Thus, an occlusion device which contains a portion which may be substantially impermeable to blood flow prior to deployment in the vasculature adds difficulty to the occlusion procedure in that the occlusion device must be oriented quite precisely in order to ensure that the covering region of the occlusion device is positioned only over the neck of the aneurysm, and not over the perforating vessels. This level of control over the positioning of the occlusion device is particularly difficult where instruments are in a size range required for intracranial therapy.

Thus, FIGS. 3A–3D illustrate an embodiment in accordance with the present invention in which the portion of the occlusion device residing over the neck of the aneurysm is made less permeable to blood flow than the remainder of the occlusion device after the occlusion device is deployed in the parent vessel. FIG. 3A illustrates that occlusion device 36, throughout its entire length, is configured in such a way so as to be significantly permeable to blood flow. In other words, the apertures in device 36 are large enough, along the entire length of device 36, to allow blood flow to pass therethrough. Occlusion device 36 is preferably deployed in lumen 12 proximate aneurysm 16 in the manner described above with respect to occlusion device 10, or in any other suitable manner.

FIG. 3A also illustrates an optional step of filling the sac of aneurysm 16 with embolic material prior to performing subsequent steps in deploying device 36. For instance, microcatheter 40 can optionally be deployed in lumen 12 and steered through the apertures in occlusion device 36, through neck 18 of aneurysm 16, and into the sac of aneurysm 16. Microcatheter 40 can then optionally be used to inject embolic agents, or other embolic material (such as coils, liquid polymer material, or other embolic material), into the sac of aneurysm 16 to promote thrombosis or simply to form a mass within aneurysm 16.

Next, with reference to FIG. 3B, an inflatable member 42 is inserted in a collapsed position through lumen 12 to the area proximate aneurysm 16. Inflatable member 42 preferably has, releasibly fastened to the exterior thereof, an occluding material or occluding substance (covering material 44) which is expandable and contractible with inflatable member 42.

Covering material 44 can be any suitable covering material or substance suitable to application to the inner surface of occlusion device 36. For example, covering material 44 can be a suitable polymer material sleeve which has adherent properties on, or an adhesive applied to, the outer surface thereof. In any case, inflatable member 42, along with covering material 44, is inserted within occlusion device 36.

FIG. 3C illustrates that, once placed inside occlusion device 36, inflatable member 42 is inflated to a configuration which has an outer diameter that approximates the inner diameter of occlusion device 36. This drives covering material 44 into contact with the inner surface of occlusion device 36. Again, covering material 44 preferably has properties causing it to adhere to the interior surface of occlusion device 36.

FIG. 3D illustrates, that once covering material 44 is deployed within occlusion device 36, inflatable member 42 is deflated so that it separates from covering material 44, leaving covering material 44 in place on the interior surface of occlusion device 36. Inflatable member 42 is then removed from lumen 12 leaving occlusion device 36 covered only in the region proximate neck 18 of aneurysm 16.

It will be understood that the longitudinal placement of covering member 44 within lumen 12 using the method described above is substantially less complex than the precise placement of an expandable occlusion device which is covered with a covering material prior to deployment. This allows covering material 44 to be carefully placed without covering any significant perforating vessels 38 which perforate parent vessel 14 in the region of aneurysm 16. In addition, this technique allows the longitudinal length of covering material 44 to be easily adjusted prior to insertion.

However, covering member 44 can also be configured to cover only a portion of the angular periphery of device 36. In that case, covering member 44 is delivered to a region of device 36 overlying neck 18, thus achieving a similar configuration to that shown in FIG. 2A.

It should also be noted that coupling material 44, or the covering portion of any of the occlusion devices previously described herein, can be coated with substances having advantageous properties. For example, the covering material can contain growth factors that enhance cell growth (e.g. growth of endothelial cells) at the neck of the aneurysm. This enhances the possibility that a lumen wall will form over the neck of the aneurysm.

Figure 4B:
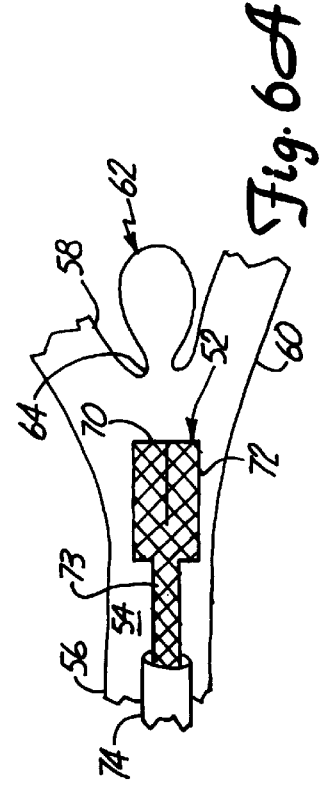
Figure 4C:
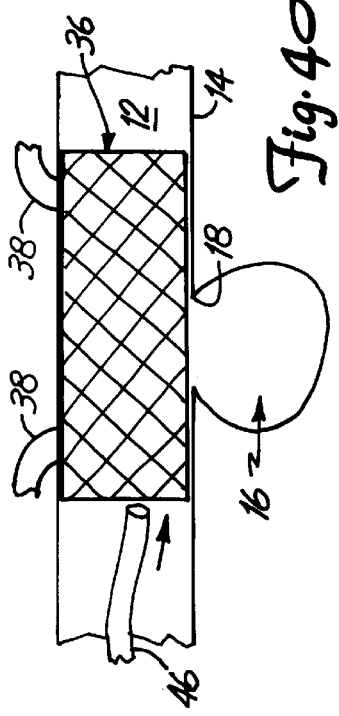

FIGS. 4A–4C illustrate another feature according to the present invention. Occlusion device 36 is covered after deployment in lumen 12, not from the inside of occlusion device 36, but instead by accessing the outer surface of occlusion device 36 from within the sac of aneurysm 16, to provide a covering in that specific area only.

After occlusion device 36 is deployed in the manner described above, or another suitable manner, microcatheter 46 is inserted through lumen 12 to the region proximate aneurysm 16. FIG. 4B illustrates that microcatheter 46 is advanced such that its distal tip 48 passes through the surface of occlusion device 36, through neck 18 in aneurysm 16 and into the sac of aneurysm 16. A liquid embolic agent (such as an embolic liquid polymer) or another suitable embolic material is injected through microcatheter 46 to substantially fill the sac of aneurysm 16. Since occlusion device 36 is formed of a material substantially permeable to blood flow, as the sac of aneurysm 16 is filled with embolic material, the blood driven from the sac of aneurysm 16 exits through neck 18 and returns to the normal blood flow through lumen 12.

Once inserted within the sac of aneurysm 16, the embolic material thickens (or changes phase) and fills the sac of aneurysm 16. As embolic material 50 is injected within the sac of aneurysm 16, it eventually fills the sac of aneurysm 16 and advances to the neck 18 where it encounters the outer surface of occlusion device 36. The embolic material fills the interstices of the wall of the occlusion device 36 in the region adjacent neck 18 of aneurysm 16 and effectively covers that portion of occlusion device 36. Microcatheter 46 is then removed and occlusion device 36 is left in place, as shown in FIG. 4C. Occlusion device 36 is covered by the embolic material behind it in the aneurysmal sac. Thus, the covering over the wall of occlusion device 36 is specifically located at the neck 18 of aneurysm 16. This effectively inhibits accidental occlusion of perforating vessels 38.

FIG. 5 illustrates another embodiment of an occlusion device 52 in accordance with the present invention. Occlusion device 52 is illustrated in lumen 54 of a vessel 56 which has a first leg portion 58 and a second leg portion 60, each of which define adjoining lumens. Aneurysm 62 is located at the portion of vessel 54 where leg 58 joins leg 60. Aneurysm 62 includes a neck portion 64 which communicates with lumen 54.

In the embodiment shown in FIG. 5, occlusion device 52 includes first portion 66 and second portion 68. First portion 66 is similar to the first portion 20 of occlusion device 10 shown in FIG. 1A, in that it is formed of a material, braid, mesh, or other substance, which has apertures therein which are large enough to be substantially permeable to blood flow. Portion 68, on the other hand, is less permeable to blood flow than portion 66 and may be substantially impermeable to blood flow. In one embodiment, portion 68 includes a covering material which is attached to occlusion device 52 to substantially cover neck 64 of aneurysm 62 when the covering portion resides on portion 68 of occlusion device 52 prior to deployment of occlusion device 52. As with the embodiment shown in FIGS. 3A–3D, the covering portion 68 can also be applied to occlusion device 52 after occlusion device 52 is deployed in lumen 54. In the instance where the covering portion 68 is applied to the interior surface of occlusion device 52, a bifurcated expandable element (or balloon) is preferably used with the covering portion attached to an appropriate region thereof so that it becomes applied to cover the neck 64 of aneurysm 62.

In the embodiment shown in FIG. 5, occlusion device 52 substantially forms a bifurcated tube including leg portions 70 and 72 and trunk portion 73. The angle defined by leg portions 70 and 72 is preferably predetermined, and includes any desired angle for the treatment of, for instance, terminal aneurysms (i.e., basilar tip aneurysms).

As with the occlusion devices described above, occlusion device 52 is preferably configured to have an insertion configuration and a deployed configuration. The occlusion device 52 transitions between the insertion configuration and the deployed configuration in response to a predetermined stimulus. In the insertion configuration, occlusion device 52 is preferably highly flexible and collapsed to a small outer diameter such that it is easily maneuverable to the location of aneurysm 62 within tortuous vasculature (such as intracranial vasculature). Once the stimulus is applied, occlusion device 52 expands to its deployed configuration shown in FIG. 5, wherein it assumes an outer diameter which closely approximates the inner diameter of lumen 54, and contacts the inner surface of lumen 54 to be retained therein.

In one preferred embodiment, the stimulus is simply the resilience of the occlusion device itself. Thus, as the occlusion device 52 emerges from a delivery catheter, it is released such that it expands to its deployed configuration.

FIGS. 6A–6D illustrate another preferred system for deployment of occlusion device 52. In one preferred embodiment, occlusion device 52 is formed of shape memory wire with a transition temperature as discussed above. FIG. 6A indicates that delivery catheter 74 is preferably moved to the region of deployment of occlusion device 52 proximate aneurysm 62. Occlusion device 52, in the insertion position, is then removed from within catheter 74.

In the preferred embodiment, the wire forming occlusion device 52 is nitinol, or other similar temperature sensitive wire. The wire defining the region where legs 70 and 72 join is preferably biased outwardly. Thus, once occlusion device 52 is deployed to the position shown in FIG. 6A and has emerged from catheter 74, occlusion device 52 assumes the shape illustrated in FIG. 6B.

The biased wire drives separation of leg portions 70 and 72 from the position shown in FIG. A to the position shown in FIG. 6B. However, the remainder of occlusion device 52 remains in the insertion (collapsed) position. With leg portions 70 and 72 spread as shown in FIG. 6B, occlusion device 52 can be easily positioned into a vessel bifurcation prior to assuming its fully deployed position.

Figure 6C:
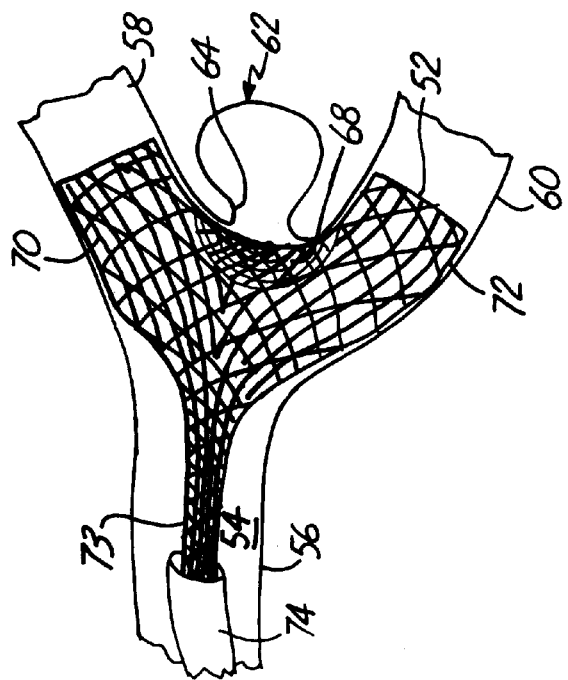

FIG. 6C illustrates that, once occlusion device 52 is positioned as shown FIG. 6B, the physician then injects saline, or another suitable solution, at or above the transition temperature, which causes leg portions 70 and 72 and trunk portion 73 to expand to have a predetermined outer diameter which closely approximates the inner diameter of legs 58 and 60 and vessel 56. FIG. 6D illustrates occlusion device 52 in the fully expanded and deployed position.

In another preferred embodiment, occlusion device 52 deploys outwardly to the position shown in FIG. 6D simply by warming to body temperature.

As with the other embodiments of occlusion devices described herein, occlusion device 52 can be used in a treatment in which aneurysm 62 is filled with embolic material, or it can be used alone, simply as a flow diverter. In either case, blood flow is diverted away from the aneurysm and blood thromboses in the aneurysm. Further, cell growth is preferably promoted over the neck of the aneurysm along the surface of occlusion device 52.

In order to obtain different rates of expansion or deployment of occlusion devices herein, a number of methods can be used. For instance, wire having substantially the same transition temperature, but different heat conductivity properties, can be used to form different occlusion devices. In that instance, the occlusion device takes a longer or shorter time to deploy because it conducts heat from the surrounding environment more slowly or more quickly than other occlusion devices made of other material. In yet another embodiment, completely different types of stimuli can be used for deploying the occlusion device.

The occlusion devices described herein can be coated or lined with any suitable material such as thromboresisting material, antiangiogenetic material such as hyloronic acid or taxol (to reduce the likelihood of in-stent remodeling of the vessel), or angiogenetic material or growth factors. The growth factors can include, for example, vascular endothelial growth factor (VEGF), platelet derived growth factor (PDGF), vascular permeability growth factor (VPF), basic fibroblast growth factor (BFGF), and transforming growth factor beta (TGF-beta).

Although the present invention has been described with reference to preferred embodiments, workers skilled in the art will recognize that changes may be made in form and detail without departing from the spirit and scope of the invention.

What is claimed is:

1. A device for treating an aneurysm in a parent vessel, the parent vessel defining a lumen and having a lumen wall, the aneurysm having a neck communicating with the lumen, the device comprising:

an occlusion device configured for deployment in the parent vessel, the occlusion device having at least a first portion and a second portion;

wherein the first portion is permeable to blood flow and arranged such that, when the occlusion device is deployed, the first portion is angularly spaced from the second portion about an outer periphery of the occlusion device;

wherein the second portion is less permeable to blood flow than the first portion; and wherein the occlusion device includes a plurality of apertures therein and wherein the apertures are substantially covered in the second portion by a covering material being less permeable to blood flow than the apertures in the first portion of the occlusion device.

2. The device of claim 1 wherein the second portion is suitable for covering the neck of the aneurysm.

3. The device of claim 1 wherein the covering material is substantially blood impermeable.

4. The device of claim 1 wherein the covering material is attached to the second portion prior to deployment of the occlusion device.

5. The device of claim 4 wherein the covering comprises a polymer material.

6. The device of claim 1 wherein the covering material comprises a covering substance wherein the occlusion device is configured to receive the covering substance on the second portion after deployment of the occlusion device.

7. The device of claim 6 wherein the occlusion device is configured to receive the covering substance on an outer surface of the second portion after deployment of the occlusion device.

8. The device of claim 6 wherein the occlusion device is configured to receive the covering substance on an inner surface of the second portion after deployment of the occlusion device.

9. A device for treating an aneurysm in a parent vessel, the parent vessel defining a lumen and having a lumen wall, the aneurysm having a neck communicating with the lumen, the device comprising:

an occlusion device configured for deployment in the parent vessel, the occlusion device having at least a first portion and a second portion wherein the first portion is permeable to blood flow and wherein the second portion is less permeable to blood flow than the first portion; and wherein the first portion comprises a braid having a first pitch and wherein the second portion comprises a braid having a second pitch, different from the first pitch of the braid in the first portion, and wherein the occlusion device is configured such that, when deployed, the second portion overlies the neck of the aneurysm.

10. A device for treating an aneurysm in a parent vessel, the parent vessel defining a lumen and having a lumen wall, the aneurysm having a neck communicating with the lumen, the device comprising:

an occlusion device configured for deployment in the parent vessel, the occlusion device having at least a first portion and a second portion;

wherein the first portion is permeable to blood flow and arranged such that, when the occlusion device is deployed, the first portion is angularly spaced from the second portion about an outer periphery of he occlusion device;

wherein the second portion is less permeable to blood flow than the first portion; and wherein the first portion comprises a braid having a first pitch and wherein the second portion comprises a braid having a second pitch, different from the first pitch.

11. A device for treating an aneurysm in a parent vessel, the parent vessel defining a lumen and having a lumen wall, the aneurysm having a neck communicating with the lumen, the device comprising:

an occlusion device configured for deployment in the parent vessel, the occlusion device having at least a first portion and a second portion;

wherein the first portion is permeable to blood flow and arranged such that, when the occlusion device is deployed, the first portion is angularly spaced from the second portion about an outer periphery of the occlusion device;

wherein the second portion is less permeable to blood flow than the first portion; and wherein the occlusion device is made of a shape memory material comprising braided Nitinol filaments, each filament having a diameter of no more than approximately 0.003 inches.

12. A device for treating an aneurysm in a parent vessel, the parent vessel defining a lumen and having a lumen wall, the aneurysm having a neck communicating with the lumen, the device comprising:

an occlusion device configured for deployment in the parent vessel, the occlusion device having at least a first portion and a second portion;

wherein the first portion is permeable to blood flow and arranged such that, when the occlusion device is deployed, the first portion is angularly spaced from the second portion about an outer periphery of the occlusion device;

wherein the second portion is less permeable to blood flow than the first portion;

wherein the occlusion device is made of a shape memory material; and wherein the occlusion device is collapsible and expands when deployed.

13. The device of claim 12 wherein the occlusion device has a geometric configuration that is collapsible and expandable.

14. The device of claim 13 wherein the occlusion device has a lumen wall that is collapsible and expandable.

15. A device for treating an aneurysm in a parent vessel, the parent vessel defining a lumen and having a lumen wall, the aneurysm having a neck communicating with the lumen, the device comprising:

an occlusion device configured for deployment in the parent vessel, the occlusion device having at least a first portion and a second portion wherein the first portion is permeable to blood flow and wherein the second portion is less permeable to blood flow than the first portion; and wherein the first portion is formed of a material defining apertures therein of a first size and wherein the second portion is formed of a material defining apertures therein of a second size smaller than the first size, and wherein the occlusion device is configured such that, when deployed, the second portion overlies the neck of the aneurysm.

16. The device of claim 15 wherein the first portion is angularly offset from the second portion about an outer periphery of the occlusion device.

17. A device for treating an aneurysm in a bifurcated parent vessel having first and second legs, the aneurysm being located at the junction of the first and second legs, the aneurysm having a neck communicating with the interior of the bifurcated parent vessel, the device comprising:

a bifurcated occlusion device configured for deployment in the bifurcated parent vessel, the occlusion device having a trunk portion, a first leg portion, and a second leg portion; and wherein the occlusion device has a non-covering portion being permeable to blood flow and a covering portion being less permeable to blood flow than the non-covering portion, the covering portion being situated at the junction of the first and second leg portions of the device such that, when the device is deployed, the second portion overlies the neck of the aneurysm.

18. A method of treating an aneurysm in a parent vessel, the aneurysm having an opening in communication with the parent vessel, the method comprising:

endovascularly moving a treatment device to a site in the parent vessel proximate the aneurysm;

deploying the treatment device in the parent vessel; and covering the opening in the aneurysm with a covering portion of the treatment device to inhibit blood flow through the opening, the covering portion being angularly offset about an outer periphery of the treatment device from a non-covering portion which allows blood flow therethrough.

19. The method of claim 18 wherein the covering portion of the treatment device includes a material portion, coupled to the treatment device prior to deployment, and being less permeable to blood flow than a remainder of the treatment device, and wherein covering comprises:

arranging the treatment device, during deployment, such that the covering portion substantially covers the opening in the aneurysm.

20. The method of claim 18 wherein covering comprises:

placing a covering material on the covering portion of the treatment device after the treatment device is deployed in the parent vessel.

21. The method of claim 20 wherein placing a covering material comprises:

inserting within an interior of the treatment device an expandable member having the covering material attached to an outer surface thereof;

expanding the expandable member to bring the covering material into contact with the interior of the treatment device; and connecting the covering material to the treatment device at least at the covering portion of the treatment device.

22. The method of claim 20 wherein placing a covering material comprises:

accessing an outer portion of the treatment device from within the aneurysm; and connecting the covering portion to the outer portion of the treatment device at least at the covering portion.

23. A method of treating an aneurysm in a parent vessel, the aneurysm having an opening in communication with the parent vessel, the method comprising:

endovascularly moving a treatment device to a site in the parent vessel proximate the aneurysm;

deploying the treatment device at the site in the parent vessel proximate the aneurysm; and covering the opening in the aneurysm with a covering portion of the treatment device to inhibit blood flow through the opening, wherein covering the opening includes placing a covering material on the covering portion of the treatment device after the treatment device is deployed in the parent vessel.

* * * * *

UNITED STATES PATENT AND TRADEMARK OFFICE
CERTIFICATE OF CORRECTION

PATENT NO. : 5,951,599
DATED : September 14, 1999
INVENTOR(S) : Jennifer J. MCCrory It is certified that error appears in the above-identified patent and that said Letters Patent is hereby corrected as shown below:

Col. 1, line 19, replace "instances" with --instance--.

Col. 1, line 28, replace "micro catheter" with --microcatheter--.

Col. 2, line 65, replace "cite" with --site--.

Col. 3, line 6, replace "12" with --14--.

Col. 4, line 49, replace "thrombose" with --thromboses--.

UNITED STATES PATENT AND TRADEMARK OFFICE
CERTIFICATE OF CORRECTION

PATENT NO. : 5,951,599
DATED : September 14, 1999
INVENTOR(S) : Jennifer J. McCrory It is certified that error appears in the above-identified patent and that said Letters Patent is hereby corrected as shown below:

Col. 5, line 20, replace "blood flow" with --bloodflow--.

Col. 5, line 39, replace "releasibly" with --releasably--.

Col. 5, line 59, after illustrates, delete ",".

Col. 6, line 65, replace "54" with --36--.

Signed and Sealed this

Twentieth Day of February, 2001

*Attest:*

NICHOLAS P. GODICI

*Attesting Officer*     Acting Director of the United States Patent and Trademark Office